(12) United States Patent
Jones (10) Patent No.: US 10,758,294 B2
(45) Date of Patent: Sep. 1, 2020

(54) ELECTROSURGICAL SYSTEM (71) Applicant: GYRUS MEDICAL LIMITED, Cardiff (GB)

(72) Inventor: Lewis Meurig Jones, Cardiff (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 1087 days.

(21) Appl. No.: 14/994,464

(22) Filed: Jan. 13, 2016

(65) Prior Publication Data
US 2016/0199125 A1 Jul. 14, 2016

(30) Foreign Application Priority Data

Jan. 14, 2015 (GB) .................................. 1500532.5
Feb. 13, 2015 (GB) .................................. 1502471.4
Feb. 13, 2015 (GB) .................................. 1502472.2

(51) Int. Cl.
*A61B 18/14* (2006.01)
*A61B 18/12* (2006.01)
*A61B 18/00* (2006.01)

(52) U.S. Cl.
CPC ...... *A61B 18/1445* (2013.01); *A61B 18/1233* (2013.01); *A61B 2018/0063* (2013.01);
(Continued)

(58) Field of Classification Search
CPC ............ A61B 18/1233; A61B 18/1445; A61B 2018/00077; A61B 2018/00083;
(Continued)

(56) References Cited

U.S. PATENT DOCUMENTS 7,150,097 B2 12/2006 Sremcich et al.
7,473,253 B2 1/2009 Dycus et al.
(Continued)

FOREIGN PATENT DOCUMENTS

AU 2006222705 10/2006
EP 1486177 12/2004
(Continued)

OTHER PUBLICATIONS

Mar. 30, 2017 Search Report issued in British Patent Application No. 1704380.3.
(Continued)

*Primary Examiner* — Michael F Peffley
*Assistant Examiner* — Tigist S Demie
(74) *Attorney, Agent, or Firm* — Oliff PLC (57) ABSTRACT

An electrosurgical system includes an electrosurgical instrument with a pair of opposing first and second jaw members (2), (3). A first sealing electrode (9) is located on the first jaw member (2), while a second sealing electrode (10) is located on the second jaw member (3). One or both of the sealing electrodes are provided with electrically conductive stop members (12), the one or more stop members maintaining a predetermined spacing between the first and second sealing electrodes when the jaw members are in their closed position. One or more insulating members (14), (17), (19) are present to prevent the conductive stop members from causing an electrical short between the first and second sealing electrodes when the jaw members are in their closed position. An electrosurgical generator (20) includes a controller (22) capable of supplying a sensing voltage between one or more of the conductive stop members (12) and a return electrode (9), (10), (18) present on one or other of the jaw members, the controller measuring the impedance between the one or more stop members and the return electrode in
(Continued)

order to measure a parameter of the tissue grasped between the jaws of the instrument.

19 Claims, 4 Drawing Sheets

(52) U.S. Cl.
CPC ........... *A61B 2018/00077* (2013.01); *A61B 2018/00083* (2013.01); *A61B 2018/00178* (2013.01); *A61B 2018/00601* (2013.01); *A61B 2018/00607* (2013.01); *A61B 2018/00642* (2013.01); *A61B 2018/00702* (2013.01); *A61B 2018/00875* (2013.01); *A61B 2018/00904* (2013.01); *A61B 2018/1455* (2013.01)

(58) Field of Classification Search
CPC ........... A61B 2018/00178; A61B 2018/00601; A61B 2018/00607; A61B 2018/0063; A61B 2018/00642; A61B 2018/00702; A61B 2018/00875; A61B 2018/00904; A61B 2018/1455
See application file for complete search history.

(56) References Cited

U.S. PATENT DOCUMENTS

| | | | |
|---|---|---|---|
| 7,877,852 B2 | 2/2011 | Unger et al. | |
| 7,922,953 B2 | 4/2011 | Guerra | |
| 8,241,284 B2 | 8/2012 | Dycus et al. | |
| 2003/0014053 A1 | 1/2003 | Nguyen et al. | |
| 2006/0052779 A1* | 3/2006 | Hammill | A61B 18/1442 606/51 |
| 2006/0224158 A1* | 10/2006 | Odom | A61B 18/1445 606/51 |
| 2006/0271035 A1 | 11/2006 | Wheeler et al. | |
| 2007/0043352 A1 | 2/2007 | Garrison et al. | |
| 2007/0265616 A1 | 11/2007 | Couture et al. | |
| 2008/0015575 A1 | 1/2008 | Odom et al. | |
| 2009/0248021 A1 | 10/2009 | McKenna | |
| 2009/0254081 A1 | 10/2009 | Allison et al. | |
| 2011/0306967 A1 | 12/2011 | Payne et al. | |
| 2012/0083783 A1* | 4/2012 | Davison | A61B 18/1445 606/45 |
| 2012/0265241 A1 | 10/2012 | Hart et al. | |
| 2013/0085496 A1 | 4/2013 | Unger et al. | |
| 2013/0226177 A1 | 8/2013 | Brandt et al. | |
| 2013/0255063 A1 | 10/2013 | Hart et al. | |
| 2014/0025073 A1 | 1/2014 | Twomey et al. | |
| 2014/0074087 A1 | 3/2014 | Yasunaga | |
| 2014/0194875 A1 | 7/2014 | Reschke et al. | |
| 2014/0371743 A1* | 12/2014 | Rothweiler | A61B 18/1445 606/41 |
| 2015/0018816 A1 | 1/2015 | Latimer | |
| 2015/0223868 A1* | 8/2015 | Brandt | A61B 18/1445 606/40 |
| 2015/0282823 A1 | 10/2015 | Trees et al. | |
| 2015/0289925 A1 | 10/2015 | Voegele et al. | |
| 2016/0270841 A1 | 9/2016 | Strobl et al. | |
| 2016/0270842 A1 | 9/2016 | Strobl et al. | |

FOREIGN PATENT DOCUMENTS

| | | |
|---|---|---|
| EP | 1795140 | 6/2007 |
| EP | 2425791 | 3/2012 |
| EP | 2687176 | 1/2014 |
| EP | 2853222 A1 | 4/2015 |
| WO | 2015/197395 A1 | 12/2015 |
| WO | 2016/149348 A1 | 9/2016 |

OTHER PUBLICATIONS

Search Report Under Sections 17 in UK Application No. GB 1600373.3, dated Jun. 15, 2016.
U.S. Appl. No. 14/992,137, filed Jan. 11, 2016, Jones, et al.
U.S. Appl. No. 14/992,193, filed Jan. 11, 2016, Thomas, et al.
U.S. Appl. No. 14/993,408, filed Jan. 12, 2016, Thomas, et al.
U.S. Appl. No. 14/993,496, filed Jan. 12, 2016, Thomas, et al.
Search Report in UK Application No. GB 1500532.5, dated Jun. 5, 2015.
Search Report in UK Application No. GB 1502472.2, dated Jul. 16, 2015.
Search Report in UK Application No. GB 1502471.4, dated Jul. 23, 2015.
Dec. 16, 2016 Search Report issued in British Patent Application No. 1600373.3.
Dec. 19, 2016 Search Report issued in British Patent Application No. 1600373.3.

* cited by examiner

ELECTROSURGICAL SYSTEM

This application claims priority to United Kingdom Applications No. 1500532.5 filed 14 Jan. 2015, No. 1502471.4 filed 13 Feb. 2015, and No. 1502472.2 filed 13 Feb. 2015, the entire contents of each of which are incorporated herein by reference.

TECHNICAL FIELD

Embodiments of this invention relate to an electrosurgical system for sealing tissue. Such systems are commonly used for the treatment of tissue in surgical intervention, most commonly in "keyhole" or minimally invasive surgery, but also in "open" surgery.

BACKGROUND TO THE INVENTION AND PRIOR ART

It is known to provide an electrosurgical instrument in which the sealing of tissue is effected by means of a pair of jaw elements. U.S. Pat. Nos. 7,473,253 & 8,241,284 are two examples of this kind of instrument. These two patents describe the provision of one or more non-conductive stop members, in order to regulate the spacing between the jaws when tissue is held therebetween.

SUMMARY OF THE INVENTION

Embodiments of the present invention attempt to provide an improvement to an electrosurgical instrument such as those described in the prior art.

Accordingly, an electrosurgical system is provided including,
a) an electrosurgical instrument including
   a handle including an actuating mechanism movable between a first position and a second position,
   a pair of opposing first and second jaw members, movement of the actuating mechanism from its first position to its second position causing at least one of the jaw members to move relative to the other from a first open position in which the jaw members are disposed in a spaced relation relative to one another, to a second closed position in which the jaw members cooperate to grasp tissue therebetween,
   a first sealing electrode located on the first jaw member,
   a second sealing electrode located on the second jaw member,
   a plurality of electrically conductive stop members disposed on one or both of the first and second sealing electrodes, the plurality of stop members maintaining a predetermined spacing between the first and second sealing electrodes when the jaw members are in their closed position, and
   one or more insulating members adapted to prevent the conductive stop members from causing an electrical short between the first and second sealing electrodes when the jaw members are in their closed position,
b) an electrosurgical generator comprising
   a source of electrosurgical energy,
   a plurality of electrical connections capable of connecting the electrosurgical instrument to the generator, such that when the jaw members of the electrosurgical instrument are in their closed position with tissue grasped therebetween, the generator is capable of supplying the electrodes with an electrosurgical current in order to seal the tissue grasped between the jaw members,
   a controller capable of supplying a sensing voltage between one or more of the plurality of conductive stop members and a return electrode present on one or other of the jaw members, the sensing voltage being less than the voltage required in order to modify tissue, the controller measuring the impedance between the one or more of the plurality of stop members and the return electrode in order to measure a parameter of the tissue grasped between the jaws of the instrument.

The electrically conductive nature of the plurality of stop members is in this way used to provide information about the tissue grasped between the jaw members. In one arrangement the sealing electrode on which the plurality of conductive stop members are disposed conveniently constitutes the return electrode. Therefore the sensing voltage is supplied between the stop members and the electrode on the same jaw member. The parameter measured by the controller is typically the presence of tissue between the jaw members. Typically a high impedance between the plurality of stop members and the sealing electrode indicates an air gap and hence the absence of tissue. Where tissue is present and in contact with both the stop member and the sealing electrode, the impedance will typically be lower as a conductive path is created through the tissue. By measuring the impedance in this way, the controller can be given an indication of whether tissue is present between the jaws.

Alternatively, the parameter measured by the controller is the degree of coagulation of the tissue between the jaw members. It is known that the impedance of the tissue is an indication of the degree of desiccation, and hence measuring the impedance between the plurality of stop members and the sealing electrode can give the controller an indication of the degree to which the tissue has been coagulated.

Additionally or alternatively, the sealing electrode opposite the one on which the plurality of conductive stop members are disposed constitutes the return electrode. In this way, the sensing voltage is supplied between the stop members and the electrode on the opposite jaw member, through the tissue grasped between the jaws. In this case, the parameter measured by the controller is typically the thickness of tissue between the jaw members. Alternatively, the parameter measured by the controller is the spacing between the jaw members. Whichever parameter is being measured, the impedance between the plurality of stop members on one jaw member and the sealing electrode on the other jaw member gives an indication of the electrical pathway between the jaws, and hence an indication of the thickness of tissue and/or the separation of the jaws.

According to one convenient arrangement, the one or more insulating members comprise a pad of insulating material located opposite a respective conductive stop member on the other sealing electrode, such that each conductive stop member contacts a respective insulating pad when the jaw members are in their closed position. In this way, the insulating pads prevent the plurality of conductive stop members from causing an electrical short between the jaws when they contact each other in their closed position.

Alternatively, the one or more insulating members is conceivably constituted by a continuous structure of insulating material circumnavigating an island of conductive material so as to isolate the island of conductive material from the remainder of the sealing electrode on which the structure is located. In one convenient arrangement, the one or more insulating members are located opposite a respective conductive stop member on the other sealing electrode, such that each conductive stop member contacts a respective isolated island of conductive material when the jaw members are in their closed position. In this way, the area of the jaw opposite each conductive stop member is isolated from the remainder of the opposite jaw, such that contact between the conductive stop member on one jaw and the isolated island of conductive material on the other jaw does not cause an electrical short between the two jaws.

Alternatively, the one or more insulating members are conveniently located surrounding each conductive stop member on the same sealing electrode, such that each conductive stop member constitutes a respective isolated island of conductive material. In this arrangement, each conductive stop member is electrically isolated from the remainder of the jaw on which it is located, with no requirement for the provision of any specific features on the opposite jaw member. As each stop member is isolated from the remainder of the jaw on which it is located, the closing of the jaw members will not cause an electrical short when the stop members contact the opposite sealing electrode.

Conceivably, the plurality of stop members each comprise a deformation in the sealing electrode on which they are located, in order to project above the surface of the remainder of the sealing electrode. As mentioned previously, this is an advantage of the use of conductive stop members, as they can be integrally formed as a part of the electrode on which they are located. Alternatively, the plurality of stop members conceivably each comprise a separate conductive member, attached to the sealing electrode on which they are located. Typically in this instance, the plurality of separate conductive members are attached to the surface of the sealing electrode on which they are located.

The instrument preferably includes a plurality of conductive stop members and a plurality of insulating members. This allows for the spacing between the jaw members to be regulated along the length thereof, as opposed to merely at one specific location. Typically, the first sealing electrode includes a plurality of conductive stop members, and the second sealing electrode includes a plurality of insulating members. Alternatively or additionally, the second sealing electrode includes a plurality of conductive stop members, and the first sealing electrode includes a plurality of insulating members. Conceivably, the first sealing electrode includes both a plurality of conductive stop members and a plurality of insulating members, and the second sealing electrode includes both a plurality of conductive stop members and a plurality of insulating members. In this way, conductive stop members are provided on both jaws, along with the insulating members to prevent shorting between the jaws.

Preferably, a plurality of conductive stop members is provided, each individually connected to the controller. This allows for individual measurements to be made at the location of each of the stop members, for example thereby giving an indication of the presence or absence of tissue at each location. With the controller able to establish exactly where the tissue is present within the jaws, the electrosurgical energy can be adjusted appropriately.

While the provision of the one or more stop members is primarily to assist in the effective sealing of tissue, the instrument typically also includes a knife selectively movable from a first position relative to the first and second jaw members to a second position relative to the first and second jaw members, in order to sever tissue grasped therebetween.

In this way, the instrument is capable of grasping tissue, sealing it, and then severing the sealed tissue to form a tissue cut without bleeding.

Embodiments of the invention further reside in an electrosurgical system including,
a) an electrosurgical instrument including
a handle including an actuating mechanism movable between a first position and a second position,
a pair of opposing first and second jaw members, movement of the actuating mechanism from its first position to its second position causing at least one of the jaw members to move relative to the other from a first open position in which the jaw members are disposed in a spaced relation relative to one another, to a second closed position in which the jaw members cooperate to grasp tissue therebetween,
a first sealing electrode located on the first jaw member,
a second sealing electrode located on the second jaw member,
a cutting member actuable to cause the cutting of tissue grasped between the first and second jaw members,
one or more electrically conductive stop members disposed on one or both of the first and second sealing electrodes, the one or more stop members maintaining a predetermined spacing between the first and second sealing electrodes when the jaw members are in their closed position, the one or more conductive stop members being separate from the cutting member, and
one or more insulating members adapted to prevent the conductive stop members from causing an electrical short between the first and second sealing electrodes when the jaw members are in their closed position,
b) an electrosurgical generator comprising
a source of electrosurgical energy,
a plurality of electrical connections capable of connecting the electrosurgical instrument to the generator, such that when the jaw members of the electrosurgical instrument are in their closed position with tissue grasped therebetween, the generator is capable of supplying the electrodes with an electrosurgical current in order to seal the tissue grasped between the jaw members,
a controller capable of supplying a sensing voltage between one or more of the conductive stop members and a return electrode present on one or other of the jaw members, the sensing voltage being less than the voltage required in order to modify tissue, the controller measuring the impedance between the one or more stop members and the return electrode in order to measure a parameter of the tissue grasped between the jaws of the instrument.

Preferably, the cutting member comprises a knife selectively movable from a first position relative to the first and second jaw members to a second position relative to the first and second jaw members, in order to sever tissue grasped therebetween. Alternatively, the cutting member comprises a cutting electrode actuable by the source of electrosurgical energy in order to supply an electrosurgical current capable of cutting tissue in contact with the cutting electrode.

Embodiments of the invention further reside in an electrosurgical instrument including,
a handle including an actuating mechanism movable between a first position and a second position,
a pair of opposing first and second jaw members, movement of the actuating mechanism from its first position to its second position causing at least one of the jaw members to move relative to the other from a first open position in which the jaw members are disposed in a spaced relation relative to one another, to a second closed position in which the jaw members cooperate to grasp tissue therebetween, a first sealing electrode located on the first jaw member, a second sealing electrode located on the second jaw member, one or more electrically conductive stop members disposed on one or both of the first and second sealing electrodes, the one or more stop members maintaining a predetermined spacing between the first and second sealing electrodes when the jaw members are in their closed position, and one or more insulating members adapted to prevent the conductive stop members from causing an electrical short between the first and second sealing electrodes when the jaw members are in their closed position, at least one of the one or more electrically conductive stop members forming part of a thermocouple capable of giving an indication of the temperature of the tissue grasped between the jaw members.

The provision of one or more electrically conductive stop members allows for them to be used as part of a thermocouple circuit, in order to measure the temperature of the tissue adjacent the stop member. There is preferably provided first and second conductors attached to the at least one stop member, the first and second conductors being formed of different metallic materials. In this way, the voltage generated by the dissimilar materials, typically different metallic alloys, can be compared with the known temperature at a reference junction, and used to calculate the temperature at the stop member. Conceivably, a plurality of electrically conductive stop members each form part of a plurality of thermocouples, capable of giving an indication of the temperature of the tissue at different locations between the jaw members.

DESCRIPTION OF THE DRAWINGS

Embodiment of the invention will now be further described, by way of example only, with reference to the accompanying drawings, in which.

DESCRIPTION OF THE EMBODIMENTS

Figure 1:
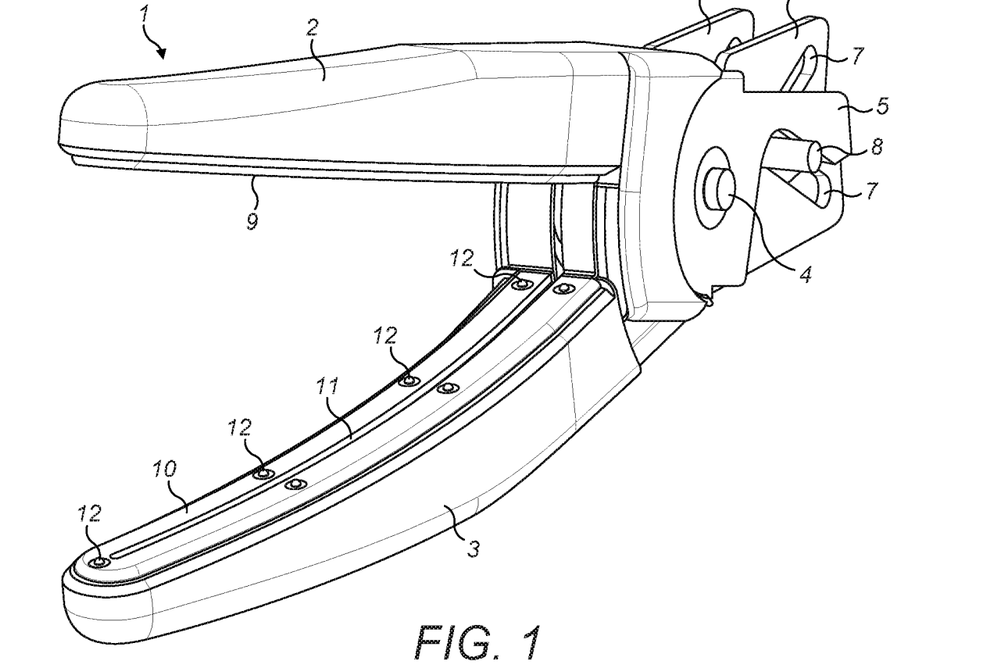
FIG. 1 is a schematic perspective view of an end effector from an electrosurgical system accordance with an embodiment of the present invention.

Referring to FIG. 1, an end effector shown generally at 1 comprises an upper jaw 2 pivotably connected to a lower jaw 3 about a pivot 4. Flanges 5 are present at the proximal end of upper jaw 2, while flanges 6 are present at the proximal end of lower jaw 3. The flanges 5 & 6 each have slots 7 through which a drive pin 8 extends, such that proximal and distal movement of the drive pin 8 (by means of a drive mechanism (not shown) causes the jaws 2 & 3 to pivot between open and closed positions.

A metallic shim 9 is present on the inward face of upper jaw 2, while a metallic shim 10 is present on the inward face of lower jaw 3. When the jaws 2 & 3 pivot into their closed position, the metallic shims 9 & 10 come into close proximity one with the other, in order to grasp tissue (not shown) therebetween.

The upper shim 9 has a generally planar surface, with the exception of a longitudinal groove (not visible in FIG. 1) running the length thereof. The lower shim 10 has a corresponding groove 11, the grooves in the shims 9 & 10 accommodating the longitudinal movement of a cutting blade (not shown). The lower shim 10 is also provided with a plurality of metallic stop members 12, disposed along the length of the shim and situated on either side of the groove 11. The stop members 12 will now be described in more detail, with reference to FIGS. 2 & 3.

Figure 2:
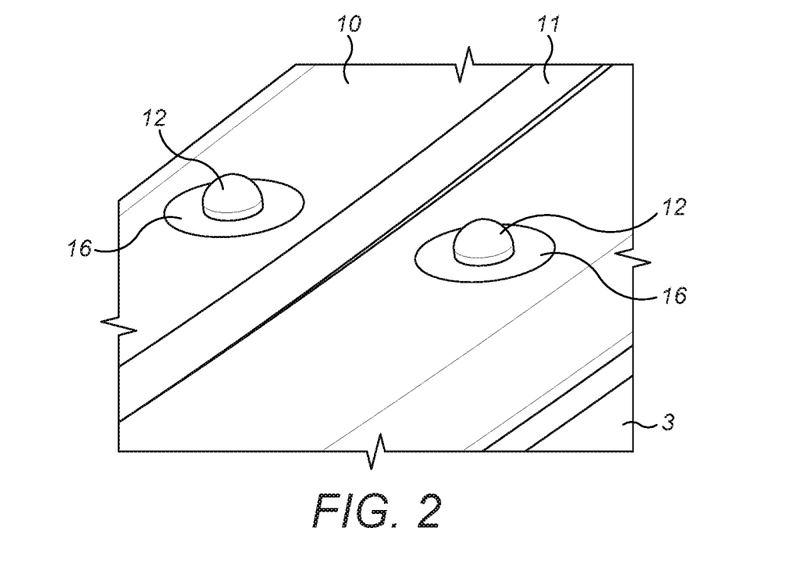
FIG. 2 is an enlarged perspective view of a part of the end effector of FIG. 1.
Figure 3:
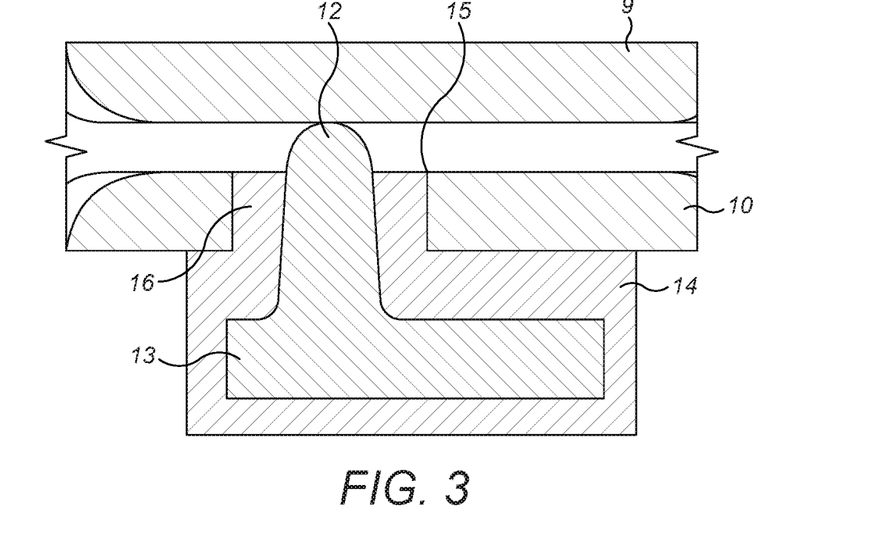
FIG. 3 is a schematic sectional view of a part of the end effector of FIG. 1.

Each metallic stop member 12 is constituted by the upper dome of a stop element 13, which is enclosed in an insulating member 14 such that it encapsulates the stop element isolating it from the remainder of the shim 10. Each insulating member 14 and stop element 13 is positioned in a corresponding aperture 15 present within the shim 10, such that the upper portion of the insulating member forms an insulating ring 16 around each stop member 12.

When the jaws 2 & 3 are moved to their closed position (as shown in FIG. 3), the stop members 12 contact the upper shim 9 maintaining a separation between the upper and lower shims of between 20 μm and about 350 μm (0.00079 inches to about 0.014 inches). In use, a coagulating electrosurgical voltage is supplied between the shims 9 & 10, and the separation of the shims ensures effective sealing of tissue grasped between the jaw members 2 & 3. In the meantime, electrical shorting between the shims is prevented, as the stop members 12 are electrically isolated such they do not carry the same electric potential as the remainder of the shim 10. The metallic stop members 12 are rigid, allowing for a consistent separation of the shim surfaces.

Figure 4:
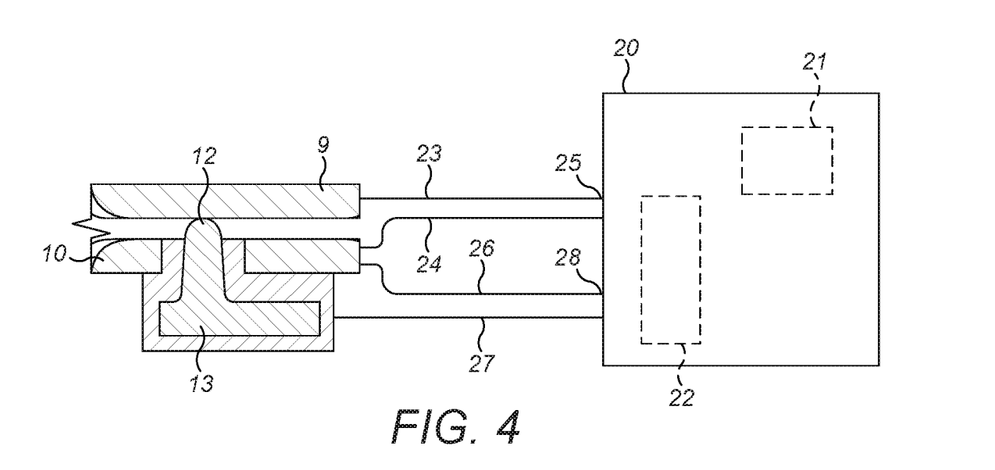
FIG. 4 is a schematic diagram showing the end effector of FIGS. 1 to 3 in combination with an electrosurgical generator.

FIG. 4 shows the use of the conductive stop members 12 to provide information about the tissue present between the jaws 2 & 3. An electrosurgical generator is shown generally at 20, and includes a source 21 of radio frequency energy and a controller 22. Leads 23 & 24 connect the upper shim 9 and the lower shim 10 to a power output 25 on the generator. Leads 26 & 27 are connected to a sensing output 28 on the generator 20. Lead 26 is connected to the lower shim 10, while lead 27 is connected to the stop member 12.

The controller 22 supplies a sensing voltage across the leads 26 & 27, and hence between the stop member 12 and the shim 10. When there is no tissue between the jaws, an air gap exists between the stop member 12 and the shim 10, providing a high impedance and hence a very low flow of current. The controller can use this to conclude that there is no tissue between the jaws. Conversely, when tissue is present between the jaws, the tissue creates a circuit between the stop member 12 and the shim 10, providing a path for current to flow therebetween and presenting a lower impedance to the generator 20. The controller can use this lower impedance to conclude that tissue is present between the jaws. Where the jaw 3 contains a plurality of stop members, they can each be wired independently to the generator, such that the presence or absence of tissue at different locations along the length of the jaw can be established. Using this information, the controller can derive parameters for the electrosurgical energy suitable for the circumstances.

The impedance between the stop member 12 and the shim 10 can also be used to derive information concerning the condition of the tissue present between the jaws. When the tissue is first presented, it will contain a relatively large amount of fluid and present a relatively low impedance between the stop member 12 and the shim 10. As electrosurgical energy is passed between the shims 9 and 10, the tissue becomes coagulated and less fluid is present. In these circumstances, the impedance presented between the stop member 12 and the shim 10 increases. By monitoring this rise in impedance, the controller 22 can establish when sufficient coagulation has taken place and advise the user to end the supply of electrosurgical energy.

Figure 5:
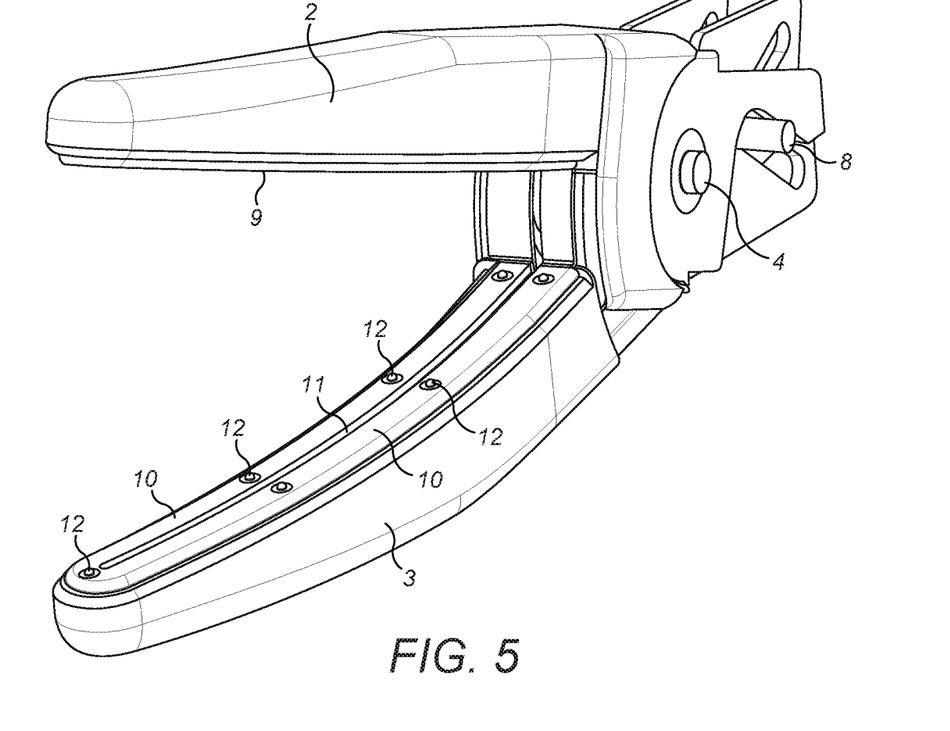
FIG. 5 is a schematic perspective view of an end effector in accordance with an alternative embodiment of the present invention.
Figure 6:
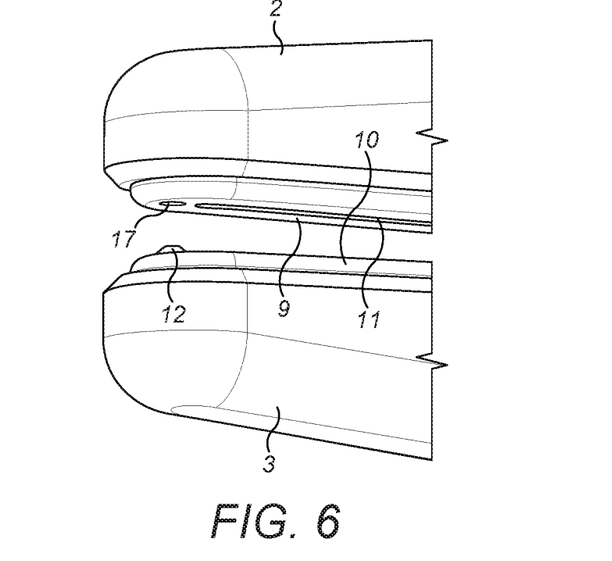
FIG. 6 is an enlarged perspective view of a part of the end effector of FIG. 4.
Figure 7:
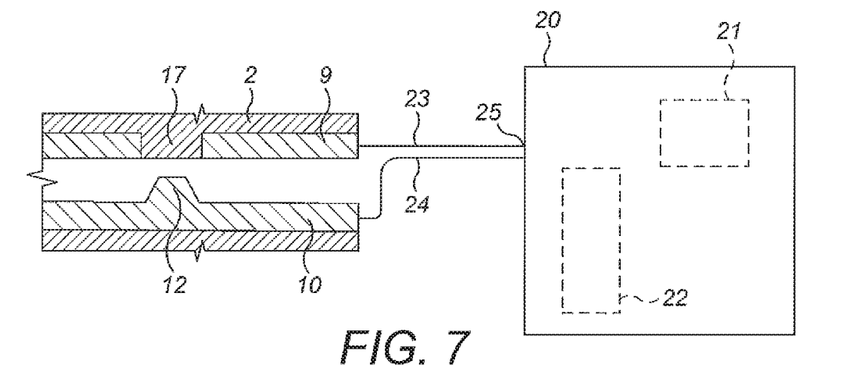
FIG. 7 is a schematic diagram showing the end effector of FIGS. 5 & 6 in combination with an electrosurgical generator.

FIGS. 5 to 7 show an alternative arrangement in which the metallic stop members 12 are mounted directly on the lower shim 10, without the provision of the insulating members surrounding the stop members. In this arrangement, insulating members 17 are provided on the upper shim 9, in corresponding relationship to each of the stop members. In this way, when the jaws 2 & 3 are closed, the insulating members 17 ensure that there is no electrical shorting between the upper shim 9 and the lower shim 10. The metallic stop members 12 ensure that the appropriate separation of the jaw members is maintained during the application of electrosurgical energy in order to seal tissue grasped between the jaws.

In FIG. 7, the leads 23 & 24 not only supply electrosurgical energy to the upper shim 9 and the lower shim 10, but also provide the leads for the sensing voltage. By monitoring the impedance between the shims 9 & 10, the presence and condition of the tissue can be determined.

Figure 8:
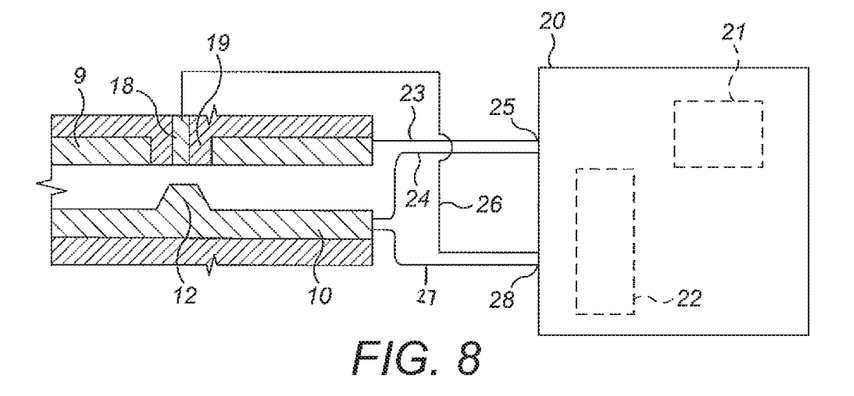
FIG. 8 is a schematic diagram showing a further alternative embodiment of end effector in combination with an electrosurgical generator.

FIG. 8 shows a further alternative, in which the metallic stop members 12 are once again mounted directly on the lower shim 10. In this arrangement, a metallic anvil 18 is located opposite each of the stop members, each metallic anvil 18 being surrounded by an insulating member 19 in order to isolate it from the remainder of the upper shim 9. When the jaws are closed, metal-to-metal contact takes place between the stop members 12 and the metallic anvils 18, with the isolation of the anvils ensuring that electrical shorting between the shims 9 & 10 is once again avoided.

As before, leads 23 & 24 connect the upper shim 9 and the lower shim 10 to a power output 25 on the generator, while leads 26 & 27 are connected to a sensing output 28 on the generator 20. Lead 26 is connected to the metallic anvil 18 on the upper shim 9, while lead 27 is connected to the lower shim 10.

The controller 22 supplies a sensing voltage across the leads 26 & 27, and hence between the stop member 12 present on the lower shim and the metallic anvil 18 opposite. When a relatively thin piece of tissue is present between the jaws, the impedance between the stop member 12 and the anvil 18 is relatively low, so the controller can conclude that the tissue between the jaws is relatively thin. Conversely, when relatively thick tissue is present between the jaws, the tissue creates a higher impedance between the stop member 12 and the anvil 18, so the controller can conclude that the tissue between the jaws is relatively thick. By calculating the thickness of the tissue and/or the separation of the jaws 2 & 3, the controller 22 can adjust the electrosurgical energy supplied to the shims 9 & 10 to create the optimum environment for the successful sealing of tissue.

Figure 9:
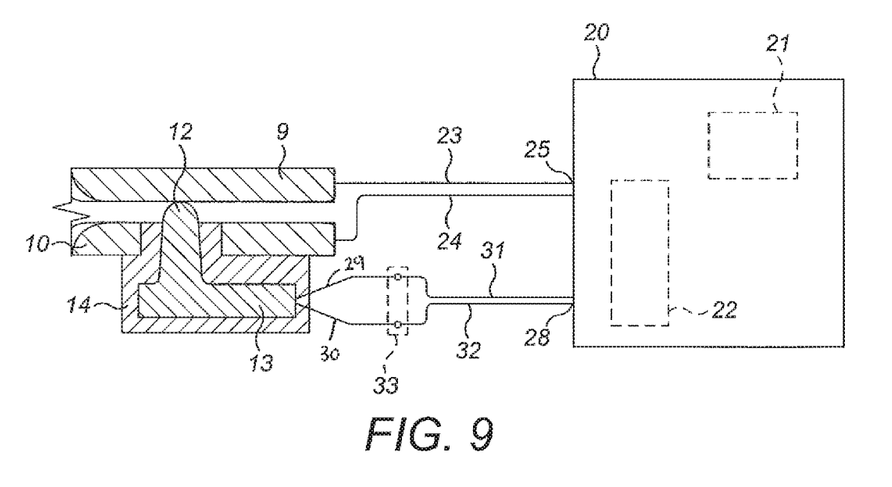
FIG. 9 is a schematic diagram showing yet another alternative embodiment of end effector in combination with an electrosurgical generator.

FIG. 9 shows an alternative arrangement in which the leads 23 & 24 connect the upper shim 9 and the lower shim 10 to a power output 25 on the generator as before. First and second conductors 29 & 30 are connected to the stop member 12, the first conductor 29 being of a first metal alloy (such as chromel) and the second conductor 30 being of a different metal alloy (such as alumel). The first and second conductors 29 & 30 are connected to ordinary copper wires 31 & 32 at a reference junction 33, and the copper wires 31 & 32 are connected to the generator 20 at the sensing output 28. The conductors 29 & 30 acts as a thermocouple, sensing the temperature of the stop member 12, hence giving an indication of the temperature of any tissue grasped between the jaws 2 & 3. If a plurality of stop members is provided along the length of the shim 10, each formed as thermocouples as described above, the temperature of the tissue at various locations along the length of the jaws can be established.

Whichever arrangement is employed, the electrical conductivity of the stop members allows for increased functionality, with various measurements possible using the electrically conductive nature of the stop members.

The invention claimed is:

1. An electrosurgical system comprising:
   an electrosurgical instrument including:
      a handle including an actuating mechanism configured to move between a first position and a second position;
      a pair of opposing first and second jaw members, movement of the actuating mechanism from the first position to the second position causing at least one of the first jaw member or the second jaw member to move from an open position so that the first jaw member is spaced from the second jaw member, to a closed position so that the first jaw member and the second jaw member are configured to grasp tissue;
      a first sealing electrode located on the first jaw member;
      a second sealing electrode located on the second jaw member;
      a plurality of electrically conductive stop members disposed on at least one of the first sealing electrode or the second sealing electrode, the plurality of stop members maintaining a predetermined spacing between the first and second sealing electrodes when the first jaw member and the second jaw member are in the closed position, and at least one of a plurality of insulating members configured to prevent the plurality of conductive stop members from causing an electrical short between the first and second sealing electrodes when the first jaw member and the second jaw member are in the closed position; and
   an electrosurgical generator comprising:
      a source of electrosurgical energy;
      a plurality of electrical connections configured to connect the electrosurgical instrument to the generator, such that when the first jaw member and the second jaw member are in the closed position, the generator is configured to supply the electrodes with an electrosurgical current to seal the tissue grasped between the jaw members; and
      a controller configured to supply a sensing voltage between at least one of the plurality of conductive stop members and a return electrode, the return electrode being one of the first sealing electrode or the second sealing electrode, the sensing voltage being less than voltage required in order to modify tissue, the controller being configured to measure an impedance between the at least one of the plurality of stop members and the return electrode to measure a parameter of the tissue grasped between the first jaw member and the second jaw member, wherein the electrosurgical generator is directly connected to both the first sealing electrode and the second sealing electrode, and is separately connected to at least one of the plurality of electrically conductive stop members.

2. An electrosurgical system according to claim 1, wherein the return electrode corresponds to one of the first sealing electrode or the second sealing electrode on which the plurality of conductive stop members are disposed.

3. An electrosurgical system according to claim 2, wherein the parameter measured by the controller is a presence of tissue between the jaw members.

4. An electrosurgical system according to claim 2, wherein the parameter measured by the controller is a degree of coagulation of the tissue between the jaw members.

5. An electrosurgical system according to claim 1, wherein the return electrode corresponds to one of the first sealing electrode or the second sealing electrode on which the plurality of conductive stop members are not disposed.

6. An electrosurgical system according to claim 5, wherein the parameter measured by the controller is a thickness of tissue between the jaw members.

7. An electrosurgical system according to claim 5, wherein the parameter measured by the controller is a spacing between the jaw members.

8. An electrosurgical system according to claim 1, wherein the one or more insulating members comprise a pad of insulating material located opposite a respective conductive stop member on the other sealing electrode, such that each conductive stop member contacts a respective insulating pad when the first jaw member and the second member are in the closed position.

9. An electrosurgical instrument according to claim 1, wherein the one or more insulating members is constituted by a continuous structure of insulating material circumnavigating an island of conductive material so as to isolate the island of conductive material from the remainder of the sealing electrode on which the structure is located.

10. An electrosurgical instrument according to claim 9, wherein the one or more insulating members are located opposite a respective conductive stop member on the other sealing electrode, such that each conductive stop member contacts a respective isolated island of conductive material when the jaw members are in their closed position.

11. An electrosurgical instrument according to claim 9, wherein the one or more insulating members are located surrounding each conductive stop member on the same sealing electrode, such that each conductive stop member constitutes a respective isolated island of conductive material.

12. An electrosurgical instrument according to claim 1, wherein the first sealing electrode includes a plurality of conductive stop members, and the second sealing electrode includes a plurality of insulating members.

13. An electrosurgical instrument according to claim 1, wherein the second sealing electrode includes a plurality of conductive stop members, and the first sealing electrode includes a plurality of insulating members.

14. An electrosurgical instrument according to claim 1, wherein the first sealing electrode includes the plurality of conductive stop members and the plurality of insulating members, and the second sealing electrode includes the plurality of conductive stop members and the plurality of insulating members.

15. An electrosurgical system according to claim 2, wherein the conductive stop members are each individually connected to the controller.

16. An electrosurgical instrument according to claim 1, wherein the instrument includes a knife selectively movable from a first position relative to the first and second jaw members to a second position relative to the first and second jaw members, in order to sever tissue grasped therebetween.

17. An electrosurgical system comprising:
an electrosurgical instrument including:
a handle including an actuating mechanism configured to move between a first position and a second position;
a pair of opposing first and second jaw members, movement of the actuating mechanism from the first position to the second position causing at least one of the first jaw member or the second jaw member to move relative to the other from an open position so that the first jaw member is spaced from the second jaw member, to a closed position so that the first jaw member and the second jaw member are configured to grasp tissue;
a first sealing electrode located on the first jaw member;
a second sealing electrode located on the second jaw member;
a cutting member configured to actuate to cut the tissue grasped between the first jaw member and the second jaw member;
an electrically conductive stop member disposed on at least one of the first sealing electrode or the second sealing electrode, the stop member maintaining a predetermined spacing between the first and second sealing electrodes when the first jaw member and the second jaw member are in the closed position, the conductive stop member being separate from the cutting member; and
an insulating member configured to prevent the conductive stop member from causing an electrical short between the first and second sealing electrodes when the first jaw member and the second jaw member are in the closed position;
an electrosurgical generator comprising:
a source of electrosurgical energy;
a plurality of electrical connections configured to connect the electrosurgical instrument to the generator, such that when the first jaw member and the second jaw member are in the closed position, the generator is configured to supply the electrodes with an electrosurgical current to seal the tissue grasped between the first jaw member and the second jaw member;
a controller configured to supply a sensing voltage between the conductive stop member and a return electrode, the return electrode being one of the first sealing electrode or the second sealing electrode, the sensing voltage being less than a voltage required in order to modify tissue, the controller being configured to measure an impedance between the at least one of the plurality of stop members and the return electrode in order to measure a parameter of the tissue grasped between the first jaw member and the second jaw member, wherein the electrosurgical generator is directly connected to both the first sealing electrode and the second sealing electrode, and is separately connected to the electrically conductive stop member.

18. An electrosurgical system according to claim 17, wherein the cutting member comprises a knife selectively movable from a first position relative to the first and second jaw members to a second position relative to the first and second jaw members, in order to sever tissue grasped therebetween.

19. An electrosurgical system according to claim 17, wherein the cutting member comprises a cutting electrode actuable by the source of electrosurgical energy in order to supply an electrosurgical current capable of cutting tissue in contact with the cutting electrode.

\* \* \* \* \*